United States Patent [19]

Alspector

[11] Patent Number: 5,346,829
[45] Date of Patent: Sep. 13, 1994

[54] DEVICE AND METHOD FOR DETECTING PRESENCE AND EXTENT OF MICRO-ORGANISMS IN A LIQUID SAMPLE OR ON A SOLID SURFACE

[76] Inventor: Benjamin Alspector, San Martin 13/8, Jerusalem 93341, Israel

[21] Appl. No.: 18,179

[22] Filed: Feb. 16, 1993

[30] Foreign Application Priority Data

Feb. 16, 1992 [IL] Israel ............................ 100964

[51] Int. Cl.⁵ .................................... C12M 1/28
[52] U.S. Cl. .............................. 435/294; 435/292;
435/298; 435/299; 422/58; 422/702
[58] Field of Search ............... 422/56, 57, 58, 102;
435/34, 294, 292, 299, 298

[56] References Cited

U.S. PATENT DOCUMENTS

| | | | |
|---|---|---|---|
| 3,563,859 | 2/1971 | Fink | 435/294 |
| 3,881,993 | 5/1975 | Frake et al. | 435/294 |
| 3,907,647 | 9/1975 | Sanderson | 435/294 |
| 3,966,552 | 6/1976 | Pagano et al. | 195/139 |
| 4,801,547 | 1/1989 | Rosenberg | 435/294 |
| 4,865,988 | 9/1989 | Gonik | 435/296 |

FOREIGN PATENT DOCUMENTS 2936294 6/1980 Fed. Rep. of Germany .
9004647 5/1990 PCT Int'l Appl. .

Primary Examiner—James C. Housel
Assistant Examiner—Lien Tran
Attorney, Agent, or Firm—Leydig, Voit & Mayer

[57] ABSTRACT

A device is provided for detecting the presence of a microorganism in a liquid sample or on a solid surface that includes a cover member which is open at least at one end thereof; a support member accommodated within the cover member capable of carrying a microorganism culture medium on one or both opposite faces thereof, which support member is movable into and out from the cover member; a handle for moving the support member into and out from the cover member; and optionally having a sampling member. A combined method for detecting the presence and extent of microbial contamination in a liquid sample and inoculation of micro-organisms by employing the device is also disclosed. This involves transferring a portion of a liquid sample to the upper part of the culture medium and dipping the lower part of said culture medium in the liquid following the steps of dipping the tip in the liquid sample; removing the tips from the liquid; pushing the support member out of the cover member by the handle for moving the support member; dipping the front part of the exposed support member in the liquid sample so as to immerse the front part of the microbial culture medium carried on the support member in the liquid; removing the device from the liquid sample; pulling the support member back into the cover member by the handle for moving the support member; and incubating the device for microbial growth.

24 Claims, 9 Drawing Sheets

DEVICE AND METHOD FOR DETECTING PRESENCE AND EXTENT OF MICRO-ORGANISMS IN A LIQUID SAMPLE OR ON A SOLID SURFACE

FIELD OF THE INVENTION

The present invention relates to devices and methods for detecting the presence and extent of microbial contamination in a liquid or on a solid surface.

BACKGROUND OF THE INVENTION

Conventionally used methods for detecting the presence and extent of microbial contamination of a liquid, particularly biological fluids such as urine, consist of immersing a dipslide which carries a solid microbial culture medium on one or both sides, into a sample of the liquid, removing the slide and inserting the same into a transport container, and incubating the slide for the microbial growth. The solid culture medium is carried on a plastic paddle, usually on both sides, and the paddle is attached to a screw-cap and inserted into a usually transparent plastic container. One major drawback of this method is that individual colonies can only be obtained within a very narrow range of contamination. Another drawback of this method is that for small volume of tested sample, an effective dipping of the dipslide is hard to achieve. Furthermore, the cap has to be unscrewed and screwed on. In addition, the presence of antibiotics in the sample, for example in urine samples from patients already under antibiotic treatment, interferes with the test, since the whole culture medium is dipped into the sample and it is well known that antibiotics interfere with the growth of micro-organisms colonies.

Another device, such as described in U.S. Pat. No. 4,801,547, is for transferring a portion of the liquid sample to a culture medium by means of a transfer member adapted between two panels carrying culture media on one or both faces. One end of the transfer member is first dipped into the sample and by pulling its other end the sample is smeared onto the culture media at the inside face of the folded panels. The volume of the applied sample is gradually reduced along the support member including the panels. The major drawback of this method is that it is hard to detect low contaminations. In this device, the micro-organisms colonies face towards the inside, which makes them hard to inspect and count. Furthermore, this device is only suitable for sampling, not for dipping, and requires use of both hands of the laboratory technician. The support member needs to be relatively long, in order to achieve the desired reduction in the volume of the applied sample.

It would therefore be desirable to provide an easy to use device, for example operable with a single hand, for detecting the presence of micro-organisms in liquid sample or on a solid surface.

It would also be desirable to provide a microbial contamination detecting device that can be used in multiple modes, for example as a conventional dipslide or for transferring of a sample, or a combination of both.

Furthermore, it is of importance to provide a device that would enable detecting wider ranges of microbial contamination.

In addition, it is desirable to enable isolation of individual micro-organism colonies, especially when the sample contains antibiotics or is highly contaminated, and to combine the quantitative accuracy of the dipping method with the qualitative advantages of isolation of individual colonies in a single device.

Another important feature is the ability to test small volume samples.

It is further important to provide a device which would reduce storage and handling space whether in shipment or during sterilization and incubation.

The present invention is directed to microbial contamination detection devices which overcome the above mentioned drawbacks and attain the desired goals.

BRIEF SUMMARY OF THE INVENTION

The present invention relates to a device for detecting the presence of a microorganism in a liquid sample or on a solid surface, comprising a cover member which is open at least at one end thereof, a support member accomodated within said cover member capable of carrying a microorganism culture medium on one or both opposite faces thereof, which support member is movable into and out from the cover member, and means for moving said support member into and out from said cover member.

One preferred embodiment the invention relates to a device for detecting the presence of a microorganism in a liquid sample or on a solid surface wherein the cover member is elongated and is open at least at the front end thereof, and comprises a slit along at least part of its length, along its longitudinal axis and the means for moving the support member comprise a handle attached to the support member at the distal end thereof and projecting out of the cover member, which handle is movable within the slit, thereby sliding the support member inside and outside the cover member through the open front end thereof.

In a preferred embodiment the cover member closed at its rear end and open at its front end.

Specific embodiments in which the handle is flexibly attached to the support member are suitable for detection of presence and extent microbial contamination on solid surfaces.

A particularly preferred embodiment of the microbial contamination detecting device according to the invention may further comprise a sampling member which may be permanently or releasably attached to the rim of the cover member, which sampling member comprises at least one inwardly bent flexible tip extending out of the cover member, so that when the support member is pulled out from or pushed into the cover member the tips touch the solid culture medium, whereby the sample is smeared onto said culture medium carried on the support member. Preferably, the sampling member comprises two flexible tips at opposite sides, slightly bent towards each other. The tips may be of different configurations. If more than one tip is used in the same device, the tips may differ in configuration in order to extend the detection range of microbial contamination, as one tip may be calibrated to deliver greater volumes of the sample liquid than the other.

In accordance with another embodiment of this invention, the cover member is open at its front end and has an opening at its rear end, the opening allowing free movement of a piston-like handle, which piston is attached to the rear end of the support member. By pushing the piston, the support member is pushed out of the cover member and by pulling the piston, the support member is pulled back into the cover member.

The invention also relates to a method for detecting the presence and extent of a microbial contamination in a liquid sample by employing a device according to the invention comprising the steps of pushing the support member out of the cover member by the means for moving the support member, dipping the exposed support member in the liquid sample so as to immerse the microbial culture medium carried on the support member in the liquid, removing the device from the liquid sample, pulling the support member back into the cover member by said means for moving the support member, and incubating the device for microbial growth.

In a particular embodiment of this method the invention relates to a method for detecting the presence and extent of microbial contamination in a liquid sample by employing a device according to the invention comprising the steps of pushing the support member out of the cover member by pushing the handle forward along the slit, dipping the exposed support member in the liquid sample so as to immerse the microbial culture medium carried on the support member in the liquid, removing the device from the liquid sample, pulling the support member back into the cover member by pulling the handle backward along the slit, and incubating the device for microbial growth.

The invention also relates to a method for detecting the presence and extend of a microbial contamination as well as inoculation of microorganisms on a culture medium in a liquid sample by transferring a portion of the liquid sample onto microbial culture medium, employing a suitable device according to the invention comprising the steps of dipping the tips in the liquid sample, removing the tips from the liquid sample, pushing the support member out of the cover member by the means for moving the support member, pulling the support member back into the cover member by the means for moving the support member; and incubating the device for microbial growth.

In a particular embodiment of this method, the invention relates to a method for detecting the presence and extent of a microbial contamination as well as inoculations of microorganism on a culture medium in a liquid sample by transferring a portion of the liquid sample onto microbial culture medium, employing a device according to the invention comprising a sampling member, comprising the steps of dipping the tips in the liquid sample, removing the tips from the liquid sample, pushing the support member out of the cover member by pushing the handle forward along said slit, pulling the support member back into the cover member by pulling their handle backward along the slit, and incubating the device for microbial growth.

Furthermore, the invention provides for a method for detecting the presence and extent of a microbial contamination as well as inoculation of microorganism on a culture medium in a liquid sample by employing a suitable device according to the invention, by transferring a portion of the liquid sample to the upper part of the culture medium and dipping the lower part of the culture medium in the liquid comprising the steps of dipping the tips in the liquid sample, removing the tips from the liquid, pushing the support member out of the cover member by the means for moving the support member, dipping the front part of the exposed support member in the liquid sample so as to immerse the front part of the microbial culture medium carried on the support member in the liquid, removing the device from the liquid sample, pulling the support member back into the cover member by the means for moving the support member, and incubating the device for microbial growth.

In a particular embodiment of this further method the invention provides for a method for detecting the presence and extent of a microbial contamination as well as inoculation of microorganism on a culture medium in a liquid sample by employing the device according to the invention comprising a sampling tip, by transferring a portion of the liquid sample to the upper part of the culture medium and dipping the lower part of the culture medium in the liquid comprising the steps of dipping the tips in the liquid sample, removing the tips from the liquid, pushing the support member out of the cover member by pushing the handle forward along the slit, dipping the front part of the exposed support member in the liquid sample so as to immerse the front part of the microbial culture medium carried on the support member in the liquid, removing the device from the liquid sample; pulling the support member back into the cover member by pulling the handle backward along the slit, and incubating the device for microbial growth.

The invention will be described in detail on hand of the attached drawings.

BRIEF DESCRIPTION OF DRAWINGS

FIG. 1-*b* is an isometric view of a cover member;

FIG. 1-*c* is an isometric view of a sampling member;

FIG. 1-*d* is an isometric view of the assembled support and cover members of FIGS. 1-*a* and 1-*b*;

FIG. 1-*e* is an isometric view of an assembled device according to the invention, including a support, cover and sampling members of FIGS. 1-*a*, 1-*b* and 1-*c*;

FIG. 1-*a*-1 is a longitudinal cross section of another embodiment of the support member;

FIG. 1-*a*-2 is a perspective view of the support member of FIG. 1-*a*-1;

FIG. 5-*c* illustrates a further embodiment of a support member suitable for use with the sampling member of FIGS. 5*a*–5*b*;

FIG. 5-*d* is a longitudinal cross section of a device with a syringe-like mechanism;

FIG. 5-*e* is a longitudinal cross section of a device as in 5-*d*, having a spring as backpushing element;

FIGS. 7-*c*, 7-*d* are cross-sections of two embodiments of the cover member with the support member therein;

FIG. 10-b a multi-stopper for multiple devices.

DETAILED DESCRIPTION OF THE INVENTION

Figure 1A:
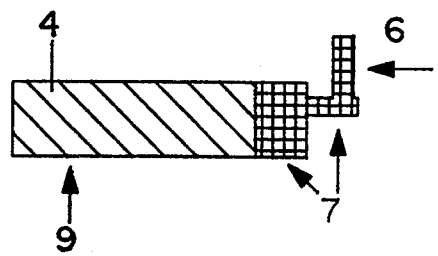
FIG. 1-*a* is a longitudinal cross section of of a support member.
Figure 1D:
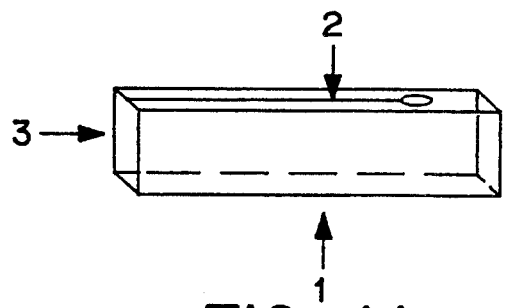
Figure 1B:
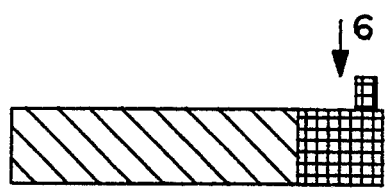
Figure 1E:
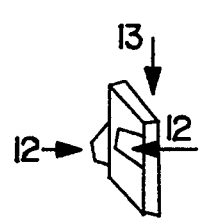
Figure 1F:
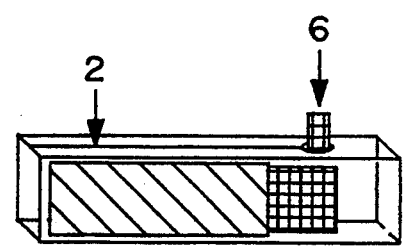
Figure 1C:
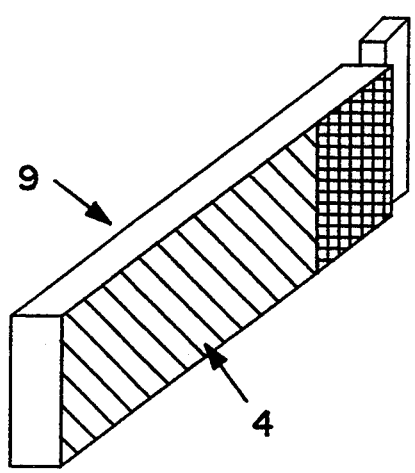
Figure 1G:
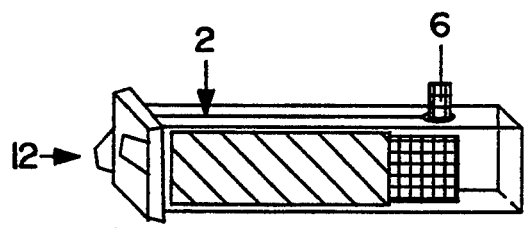
Figure 2A:
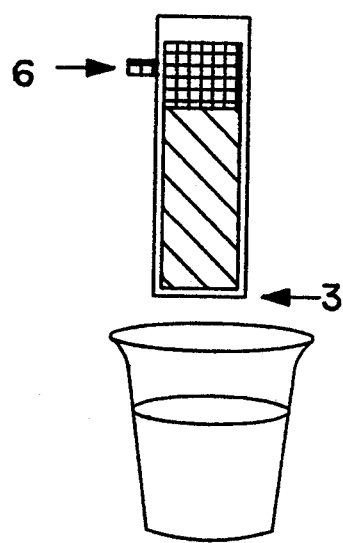
FIGS. 2*a*, 2*b*, 2*c* and 2*d* are a schematic presentation of dipping protocol.
Figure 2B:
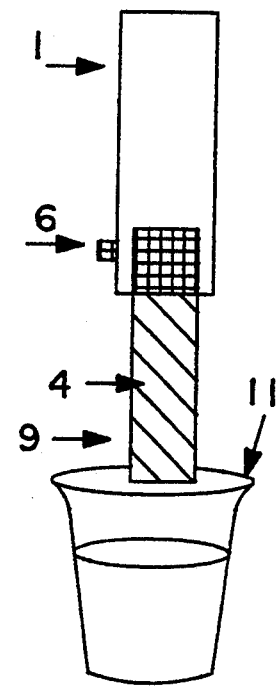
Figure 2C:
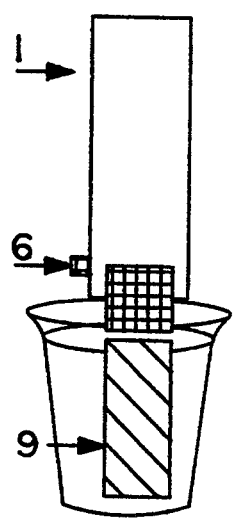
Figure 2D:
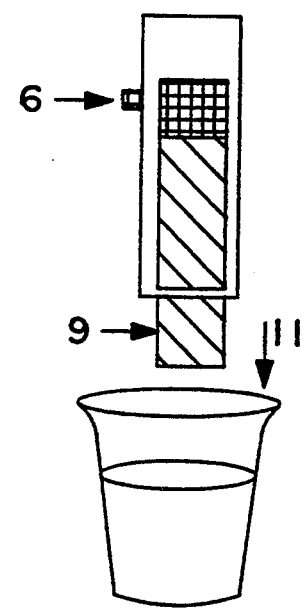
Figure 3A:
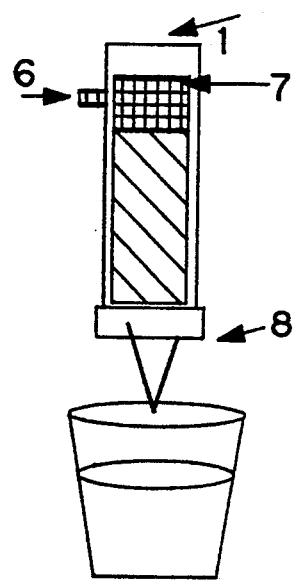
FIGS. 3*a*, 3*b*, 3*c*, and 3*d* are schematic presentation of sampling protocol.
Figure 3B:
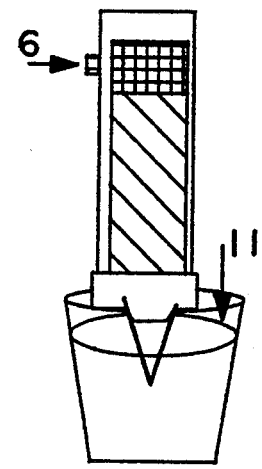
Figure 3C:
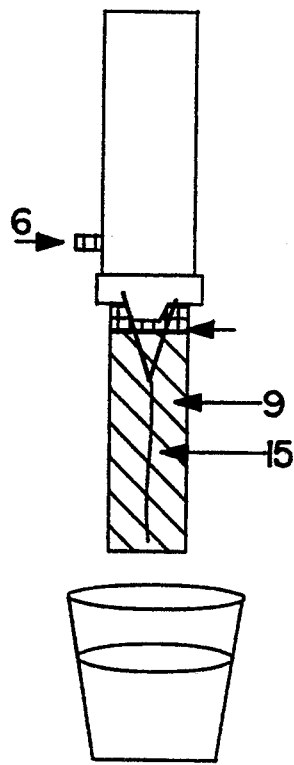
Figure 3D:
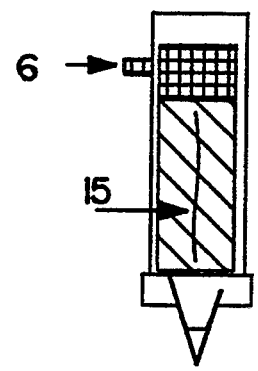
Figure 4A:
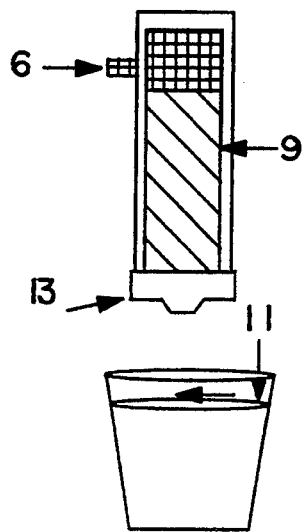
FIGS. 4*a*, 4*b*, 4*c* and 4*d* are a schematic presentation of a combined dipping and sampling protocol.
Figure 4B:
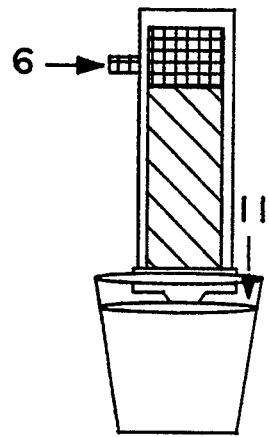
Figure 4C:
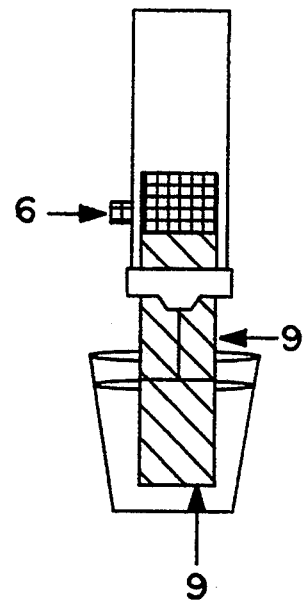
Figure 4D:
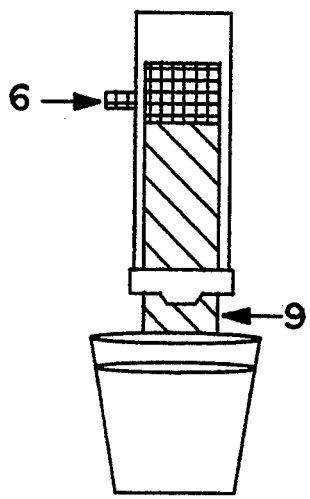
Figure 4E:
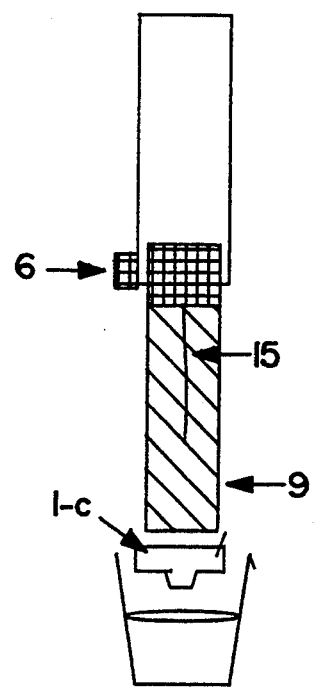
FIG. 4-*e* illustrates the removal of the sampler member.

The invention relates to a device for detecting the presence of a micro-organism in a liquid sample or on a solid surface, comprising an elongate cover member which is open at least at the front end thereof, the cover member comprising a slit along at least part of its length, along its longitudinal axis, a support member capable of carrying a micro-organism solid culture medium on one or both opposite sides thereof and a handle which is integrally or releasably attached thereto at the distal end thereof and protruding out of the cover member, which handle is movable within the slit, thereby sliding the support member inside and outside the cover member through the open front end thereof.

The cover member may be made of any suitable material, preferably plastic material. Most preferred is a cover member made from transparent plastic material, which enables the inspection and count of the micro-organism colonies on the culture medium. The cover member may be of any suitable cross-section, round, rectangular, polygonal or oval. Rectangular cover member are preferred for several reasons, for examples space saving in storage or transport and also during sterilization and incubation. In order to avoid smearing of the microbial colonies once formed, the side panels of the cover member should preferably be spaced from the culture medium bearing support member. Such spacing prevents contact between the microbial flora and the side panels of the cover member during incubation, and particularly when the support member is pushed out of the cover member for further evaluation of the microbial colonies formed. The slit in the cover member, along the longitudinal axis thereof, may be along the whole or part of the length of the cover member, according to the specific embodiment. In principle, when the cover member is open at only the front end thereof, the slit is along part thereof. The slit is preferably narrower than the thickness of the support member, reducing environmental contamination. In the preferred embodiment of a rectangular cover member, the slit is preferably on the narrow face of the cover member. This enables using support members which have a larger area for carrying the microbial culture medium. In embodiments designed for combined dipping and sampling, the slit may have a semi-stop, preferably at about the middle thereof.

In another embodiment the cover member has no slit. In this embodiment, the means for moving the support member are a piston-like handle attached to the support member via an opening at the rear end of the cover member. The piston-like handle may optionally be equipped with a spring.

The support member is generally designed to be comfortably accomodated within the cover member. The support member is preferably spaced apart from the side panels of the cove member, as described above. Thus, the side faces of the support member which carry the solid microbial culture medium may have different configurations. In case of a rectangular cover member, support members having rectangular faces are preferred. The support member is essentially flat, carrying the microbial culture medium on the flat faces thereof. Preferably, the flat sides of the support member are designed as shallow recesses, the solid culture medium being contained in the recesses.

The means for moving the support member may be any suitable means, particularly a paddle-like or piston-like handle. This handle member is attached to the support member at the distal end thereof. The handle may be rigidly of flexibly attached to the support member. Embodiments in which the handle is flexibly attached to the support member are particularly suitable for detecting the presence and extent of microbial contamination on a solid surface, enabling contacting the culture medium carrying portions of the support member with the solid surface to be monitored. The handle has a bent arm which is attached to the support member via the slit and a gripping part, protruding out from the cover member via the slit. When the handle is moved forward or backward within the slit, the support member slides into or out of the cover member.

The sampling member, which comprises at least one flexible tip slightly bent inwardly, may be permanently or releasably attached to the cover member at the front end thereof. The sampling member is preferably a frame, to which the tips are attached. The frame preferably has a cross-section similar to that of the cover member and is dimensioned to fit the open end of the cover member. The sampling member may be removed from the cover member or slightly displaced, by completely pushing the arm attached to the support member or it can be pushed forwards and backwards by a similar mechanism as the support member, or can be manually removed after use. It is preferred that the tips are removable so as not to scratch the solid culture medium on the support member when it is initially inserted into the support member. Such scratches on the culture medium may hinder the test. Furthermore, when incubation is completed the support member is pushed out of the cover member for inspection and harvesting of the colonies for further tests and it is important that the tips do not smear the bacterial colonies.

Alternatively, the sampling member may consist of an essentially U-shaped member, to the arms of which said flexible tips are attached. The U-shaped member may be permanently or releasably hingedly attached to the cover member, near the front end thereof. This preferred embodiment enables inoculation of the sample to be monitored on the microbial culture medium in two different paths. This is an important feature since, for example, when the sample is found to be heavily microbially contaminated, it is often necessary to further isolate the microorganisms which were present. Initial inoculation in an elongated path facilitates isolation. The long inoculation path is superior as the volume of the liquid sample applied to the culture medium gradually decreases and the longer the path, the higher is the dilution achieved, broadening the detection range. In addition, a larger quantity of the sample may be inoculated on the same quantity of culture medium, extending the detection range.

FIG. 1-a is a longitudinal view of a paddle-like support member (9), carrying solid culture medium (4). The two faces of paddle (9) are preferably designed as shallow recesses, containing the solid culture medium (4). A bent handle (6) is attached to the support member (9), preferably via a spacer element (7). FIG. 7-a illustrates a cross section of a support member having the two shallow recesses (9a,9b) for containing the culture medium (4a,4b), as seen in FIG. 7-b.

FIG. 1-a-1 is a longitudinal cross-section of another embodiment of the support member (9) and FIG. 1-a-2 is a perspective view of this embodiment.

FIG. 1-b illustrates a rectangular cover member (1) having an open front end (3) and a slit (2), on the narrow face, along the longitudinal axis thereof.

In order to avoid smearing of the microbial colonies once formed, the side panels of the cover member should preferably be spaced from the culture medium bearing support member. Such spacing prevents contact between the microbial flora and the side panels of the cover member during incubation, and particularly when the support member is pushed out of the cover member for further evaluation of the microbial colonies formed. Two preferred cross-sections of the cover member are depicted in FIGS. 7-c (oval) and 7-d (rounded polygonal).

FIG. 1-c illustrates a sampling member that may be permanently or releasably attached inside or outside the cover member. The sampling member comprises a frame (13), to which flexible tips (12) are connected. Tips (12) are slightly bent toward one another. The frame (13) preferably has a cross-section similar to that the cover member (1) and is so dimensioned as to fit the cover member. The sampling member may be completely removed, as further illustrated in FIG. 4-e or partly displaced, as further illustrated in FIG. 8-b.

FIG. 1-d illustrates a partly assembled device according to the invention. The support members illustrated in FIGS. 1-a and 1-a-1 are inserted into the cover member (1), handle first, via front opening (3) and can slide into and out from the cover member (1) by pushing or pulling the handle (6) along the slit (2) on the narrow face of the cover member, into which the handle (6) is inserted, said slit (2) serving as a guide track for handle (6). Thus, handle (6) serves as a push-pull button for the support member. The handle (6) is at the side opposite to the front opening 3. This figure illustrates the device in a closed position. The device illustrated in this figure can be used for dipsliding.

FIG. 1-e illustrates an assembled device comprising a cover member (1), a support member (9) and a sampling member (8).

In the following description of the methods of the invention, reference will be made to devices in which the cover member has a slit along its longitudinal axis and the means for moving the support member are a paddle-like handle. However, the methods of the invention may be carried out in a similar manner also by other embodiments of the device according to the present invention.

FIGS. 2-a to 2-d illustrate the method of using the device of FIG. 1-d, which is used as a dipslide in a vial (11) filled with sample liquid. As may be seen in FIG. 2-a, at the beginning of the protocol the device is in a closed position, that is, handle (6) is at its uppermost position and the support member (9) is wholly accomodated within the cover member (1). As seen in FIG. 2-b, the support member (9) is pushed out of the cover member by pushing handle (6) in the direction of the front opening (3), the support member (i) is then immersed in the liquid sample contained in vial (11), as in FIG. 2c, whereby the culture medium (4) is covered with the liquid to be tested, handle (6) now assuming its lowermost position. As illustrated in FIG. 2-d, the supporting member is pulled back into the cover member, by means of handle (6), back to the position illustrated in FIG. 2-a. FIG. 9-a depicts the microbial colonies which may be formed on the culture medium by employing this dipping protocol. As may be seen in this figure, colonies are homogeneously spread over the entire area of the culture medium.

FIG. 3 presents another mode of operation in which the device is used as sample transfer unit. In FIG. 3-a, a closed device in accordance with an embodiment as illustrated in FIG. 1-e, is brought to close proximitity with the surface of the liquid sample contained in vial (11), tips (12) are partly dipped into the liquid, the handle (6) being maintained at its uppermost position. After the dipping of tips (12), the whole device is removed from the liquid. The support member (9) is then pushed out of the cover member (1) by pushing the handle (6) to a lower position, whereby the sample is smeared (15) on the solid culture media (4), carried on the support member (9). The support member (9) is now pulled back into the cover member (1), to assume the closed position illustrated in FIG. 3-d, by pulling handle (6) back to its uppermost position. It may be noted, referring to FIG. 3-c, that the handle is to be pushed down to a lower position than its uppermost position, not necessarily it lowermost position. FIG. 9 b depicts the microbial colonies which may be formed on the culture medium by employing this transfer protocol. As may be seen in this figure, at the beginning of the inoculation path colonies are more crowded while their number is gradually reduced going up along the inoculation path, as the amount of liquid on the sampling tips diminishes.

FIG. 4 demonstrates another protocol in which the device is used in a combined mode, i.e., partly as a dipslide and partly for a sample transfer. In FIG. 4-a, the device is first brought to close proximity with the surface of the liquid. In FIG. 4-b, tips (12) are partly dipped into the liquid contained in vial (11). The whole device is removed from the liquid and the support member (i) is pushed out, by means of handle (6). This causes the support member to be fully smeared with the sample liquid, as in the sampling protocol illustrated in FIG. 3. The support member 9 is then partly dipped into the sample, while the upper part which has not been dipped, remains smeared (15). FIG. 9-c depicts the microbial colonies which may be formed on the culture medium by employing this combined dipping-transfer protocol. As may be seen in this figure, the lower part of the culture medium is homogenously crowded with colonies, as in the dipping method, while in the upper part the picture is similar to that obtained with the transfer protocol. If the sample is heavily contaminated, a confluent growth of colonies is obtained. This makes it difficult to observe and isolate individual colonies. In such cases simulataneous isolation of colonies is of great advantage.

FIG. 4-e illustrates the removal of the sampling member after the support member is completely pushed out of the cover member, by further pushing down handle (6). The sampling member may also be only displaced, by further somewhat pushing down said handle (not illustrated). The sampling member may also be removed manually when the support member is inside or outside the cover member.

Figures 5A, 5B:
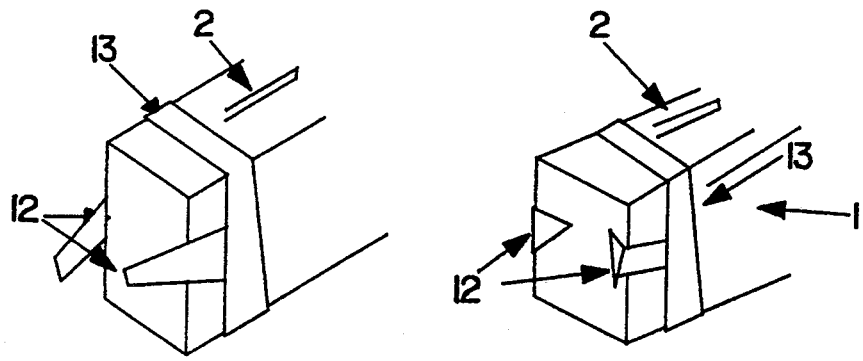
FIGS. 5-*a*, 5-*b* are perspective views of another embodiment of a sampling member, FIG. 5-*a* presenting an initial position and FIG. 5-*b* presenting the tips after sampling has been completed.
Figure 5C:
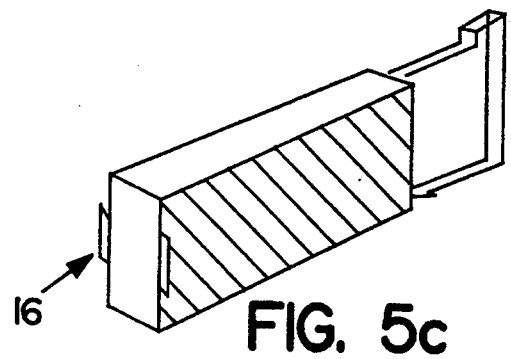
Figure 5D:
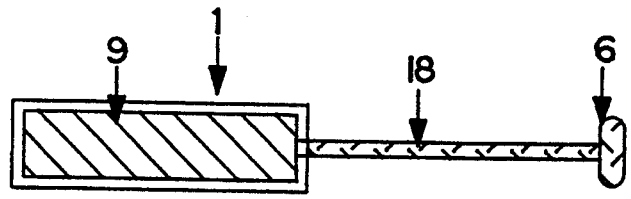
Figure 5E:
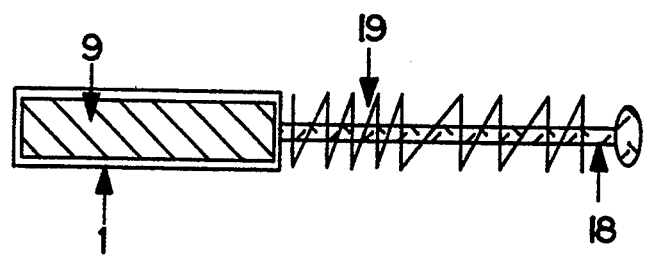

FIGS. 5a to 5c illustrate additional embodiments of the sampling member of the present invention. FIG. 5-a depicts the sampling member, before use, and FIG. 5-b the sampling member after use, in which the tips 12 are bent inwards, onto the cover member (1). This is accomplished by also providing support member (9) with extended margins (16), as may be seen in FIG. 5-c.

FIG. 5-d presents another embodiment of the moving means in which the support member (9) is pushed and pulled by a piston (18). In this embodiment, the cover member (1) has an opening at the rear side thereof, and the piston is attached to the rear end of the support member and extends out of the cover member (1) via the opening.

FIG. 5-e presents yet another embodiment in which a spring (19) is used as a back pushing member. The support member is pushed outside the cover member by pushing the piston (18), when the piston is released, the support member is automatically pulled back inside the cover member.

Figure 6:
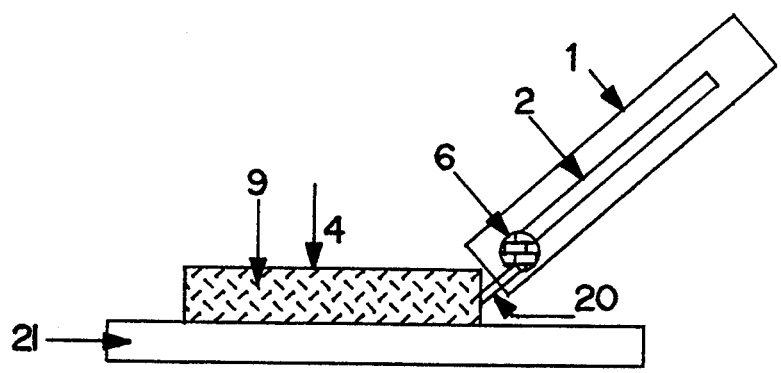
FIG. 6 illustrates an embodiment suitable for surface monitoring.
Figure 7A:
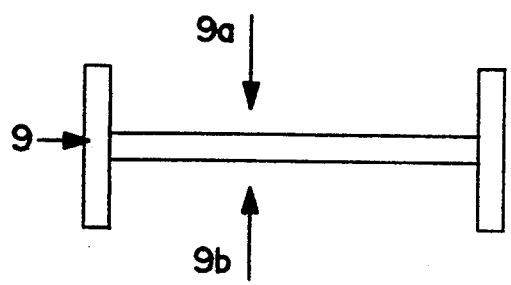
FIGS. 7-*a*, 7-*b* are cross-sections of a further embodiment of the support member of the invention.
Figure 7B:
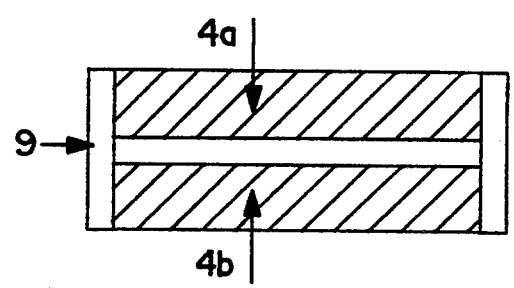
Figure 7C:
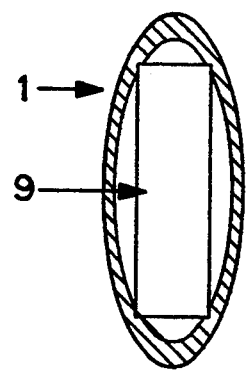
Figure 7D:
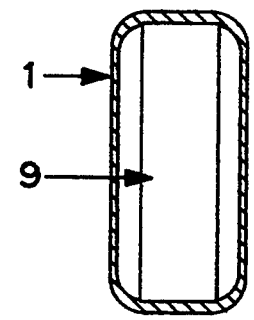

FIG. 6 presents the use of the device for surface monitoring. The device comprises a flexible element (20) connecting the handle (6) to the support member (9). When the support member is fully pushed out, its faces bearing the culture media may be brought into good contact with a surface (21) to be monitored, and then pulled back into the cover member.

Figure 8A:
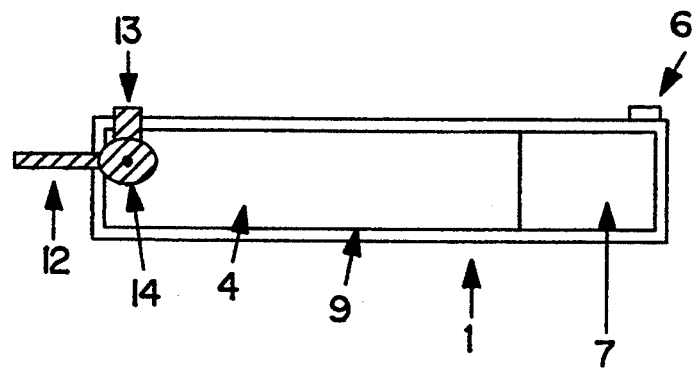
FIGS. 8*a*, 8*b* and 8*c* are side views of a device according to the present invention, with a particular sampling member.
Figure 8B:
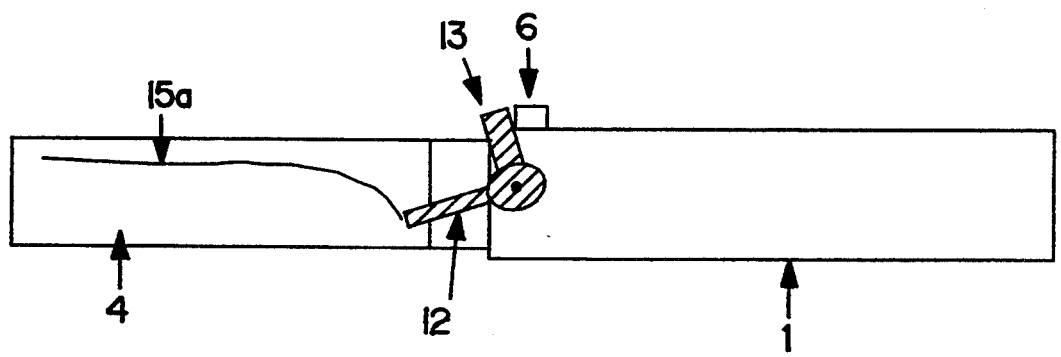
Figure 8C:
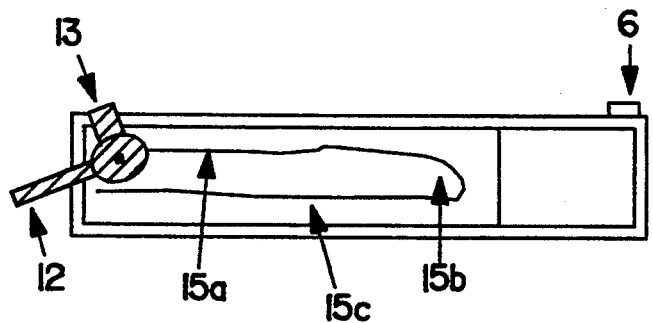
Figure 9A:
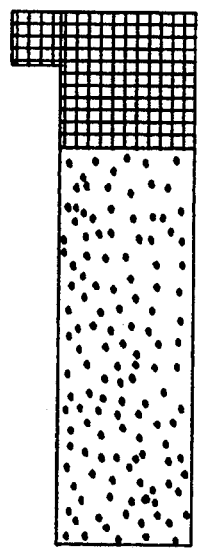
FIGS. 9a, 9b, 9c and 9d depict microbial growth on the culture medium which may be obtained by the different devices and methods of the invention.
Figure 9B:
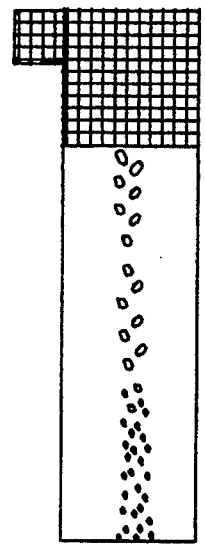
Figure 9C:
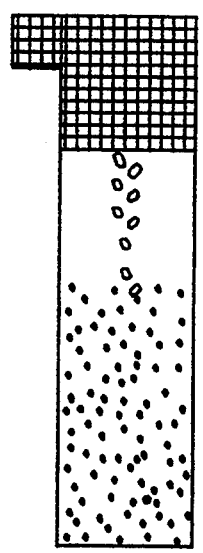
Figure 9D:
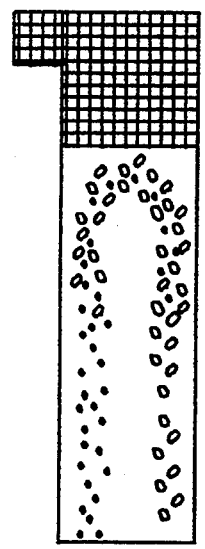

FIGS. 8a to 8c illustrate a device according to the present invention comprising a particular embodiment of the sampling member. As may be seen in FIG. 8-a, the sampling member (13) has an essentially U-shaped configuration, and has flexible tips (12) permanently or releasably attached thereto. The sampling member is permanently or releasably hingedly (14) attached to cover member (1), near the front end thereof. As may be seen in FIG. 8-b, after the tips (12) were dipped in the liquid sample, when support member (9) is pushed out of the cover member by handle (6), a first path of inoculation (15a) is formed on the culture medium, the sampling member is displaced forwards, by further pushing the moving means (6), causing tips (12) to assume a new position, forming a further inoculation path (15b). When moving means (6) are pulled back to the initial position, pulling support member (9) back into the cover member, an additional inoculation path is formed (15c) and the inoculation cyclic path is completed. FIG. 9-d depicts the microbial colonies which may be formed by using this embodiment.

Figure 10A:
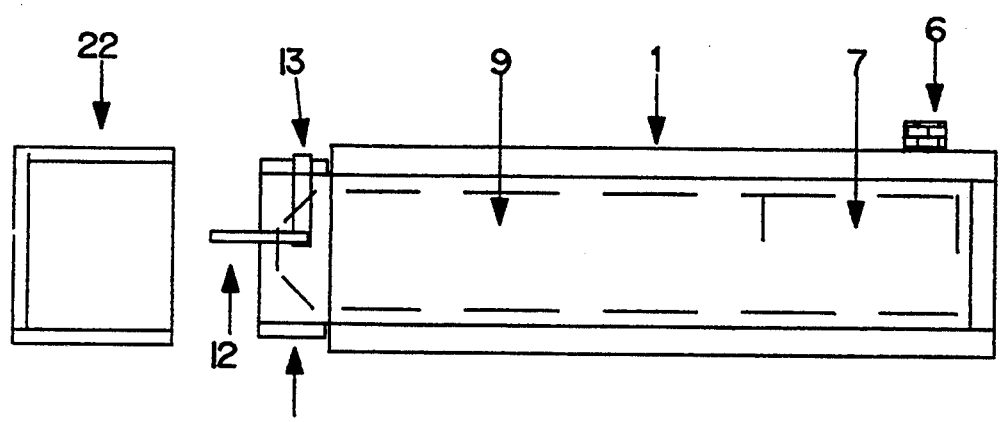
FIG. 10-a illustrates a stopper for a device according to the invention.
Figure 10B:
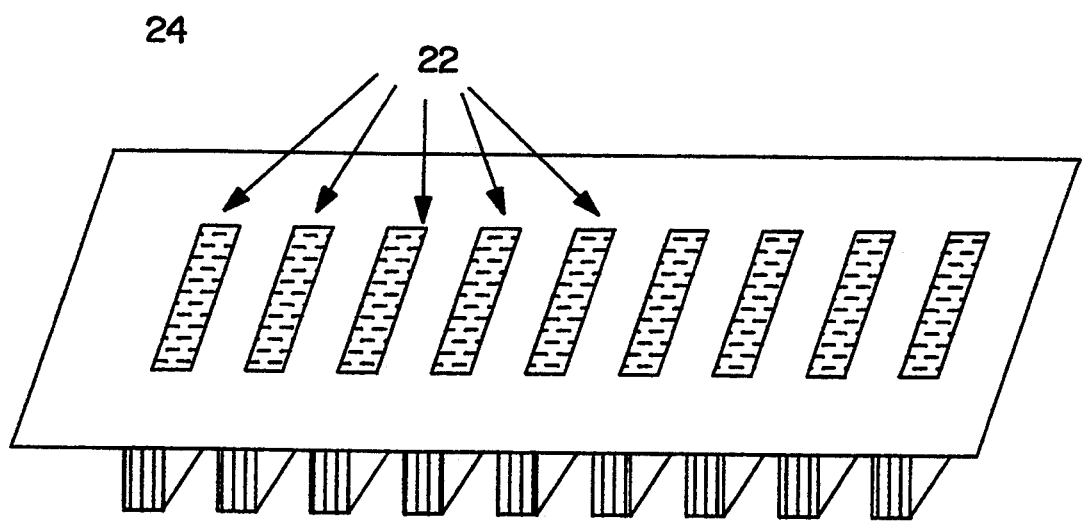

The devices according to the present invention may be equipped with a non-integral cap, (22) for covering the open front end of the cover member. Such cap, or stop member, is illustrated in FIG. 10-a. It is also possible to combine multiple stop members, as shown in FIG. 10-b. The illustrated multi-stop device may serve for holding and/or storing the devices according to the invention during shipment or during the incubation or sterilization.

I claim:

1. A device for detecting the presence of a microorganism in a liquid sample or on a solid surface, comprising:
    an elongated cover member which is open at least at one end thereof and having a slit in a wall of said cover member from said open end and extended along at least part of its longitudinal axis;
    an elongated support member accommodated within said cover member for carrying a microorganism culture medium on one or opposite surfaces thereof, which support member is movable into and out from said cover member; and
    means for facilitating movement of said support member into and out from said cover member comprising a handle attached to said support member at the one end thereof and projecting out of said cover member, which handle is movable within said slit, thereby sliding said support member into and out of said cover member through said open end.

2. A device according to claim 1 wherein said support member carries said culture member on opposite surfaces thereof.

3. A device according to claim 1 wherein said cover member has a rectangular cross section.

4. A device according to claim 1 wherein said cover member has an oval or polygonal cross section.

5. A device according to claim 1 wherein said support member is essentially flat, said culture medium being carried on the at least one flat surface thereof.

6. A device according to claim 5 where said support member has recesses on the at least one flat surface thereof, said culture medium being contained in said recesses.

7. A device according to claim 1 wherein said cove member is transparent.

8. A device according to claim 1 wherein said cover and support members are made from a plastic material.

9. A device according to claim 1 wherein said slit is narrower than the thickness of said support member.

10. A device according to claim 1 further comprising a non-integral cap, for covering the open end of said cover member.

11. A method for detecting the presence and extent of a microbial contamination in a liquid sample by employing the device according to claim 1 comprising the steps of:
    pushing said support member out of said cover member to expose said support member by pushing said handle forward along said slit;
    dipping said exposed support member in said liquid sample so as to immerse said culture medium carried on the support member in said liquid;
    removing the device from said liquid sample;
    pulling said support member back into said cover member by pulling said handle backward along said slit; and
    incubating the device for microbial growth.

12. A method for detecting the presence and extent of a microbial contamination on a solid surface by employing the device according to claim 1 comprising the steps of:
    pushing said support member completely out of said cover member by pushing said handle forward along said slit;
    contacting the exposed microbial culture on said support member with said solid surface;
    removing the device from the solid surface;
    pulling said support member back into said cover member by pulling said handle backward along said slit; and
    incubating the device for microbial growth.

13. A device according to claim 1 wherein said device is capable of quantitatively detecting the presence of a microorganism.

14. A device for detecting the presence of a microorganism in a liquid sample or on a solid surface, comprising:
    an elongated cover member having an opening at least at one end thereof and having a slit in a wall of said cover member from said open end and extended along at least part of its longitudinal axis;
    an elongated support member accommodated within said cover member for carrying a microorganism culture medium on one or opposite surfaces thereof, which support member is movable into and out from said cover member through said at least one opening;

means for facilitating movement of said support member into and out from said cover member comprising a handle attached to said support member at one end thereof and projecting out of said cover member, which handle is movable within said slit, thereby sliding said support member into and out of said cover member through said open end; and a sampling member attached to said cover member at said opening through which said support member is movable, comprising at lest one flexible tip extending outwardly from said cover member, which tip is bent inwardly, so that when the support member is pulled out from or pushed into said cover member said tip touches said culture medium, whereby a sample is smeared on said culture medium carried on said support member.

15. A device according to claim 14 wherein said sampling member comprises a frame to which said tips are attached, said frame having a cross section similar to that of the cover member and dimensioned so as to fit said cover member when attached thereto.

16. A device according to claim 15 wherein said sampling member comprise two or more flexible tips, on the same or opposite sides of said frame, which are bent inwards.

17. A device according to claim 14 wherein said sampling member is permanently or releasably hingedly attached to said cover member.

18. A method for detecting the presence and extent of a microbial contamination in a liquid sample and inoculation of microorganism by transferring a portion of said liquid sample onto a microbial culture medium, employing the device according to claim 14 comprising the steps of:
dipping said tips in said liquid sample;
removing said tips from the liquid sample;
pushing said support member out of said cover member by pushing said handle forward along said slit for a distance sufficient to allow the tips to contact the support member;
pulling said support member back into said cover member by pulling said handle backward along said slit; and
incubating the device for microbial growth.

19. A method for detecting the presence and extent of a microbial contamination in a liquid sample and inoculation of microorganisms by transferring a portion of said liquid sample a part of said culture medium and dipping another part of said culture medium in said liquid employing the device according to claim 14 comprising the steps of:
dipping said tips in said liquid sample;
removing said tips from said liquid sample;
pushing said support member out of said cover member by pushing said handle forward along said slit for a distance sufficient to allow the tips to contact the support member and that a part of the support member extend beyond the tips;
dipping the extended part of said support member in said liquid sample so as to immerse said culture medium carried on the extended part of said support member in said liquid;
removing the device from said liquid sample;
pulling said support member back into said cover member pulling said handle backward along said slit; and
incubating the device for microbial growth.

20. A method employing the device according to claim 14, comprising the steps of:
dipping said tips in said liquid sample;
removing the tips from said liquid sample;
pushing said support member out of said cover member by pushing said handle forward along said slit to expose said support member;
dipping a part of said exposed support member in said liquid sample so as to immerse said culture medium carried on the support member in said liquid;
removing the device from the liquid sample;
pulling said support member back into said cover member by pulling said handle backward along said slit; and
incubating the device for microbial growth.

21. A method according to claim 18 wherein the sampling member is removed from the device after sampling.

22. A device according to claim 14 wherein said at least one flexible tip has a tapered end.

23. A device according to claim 14 wherein said sampling member is releasably attached to said cover member.

24. A device according to claim 30 wherein said elongated support member carries the culture medium on at least one surface thereof.

* * * * *